(12) United States Patent
Somers et al.

(10) Patent No.: US 7,141,544 B2
(45) Date of Patent: Nov. 28, 2006

(54) STABILIZATION OF PHARMACEUTICAL PROTEIN FORMULATIONS WITH SMALL PEPTIDES

(75) Inventors: Fabian Somers, Neupre (BE); Dirk Faict, Assenede (BE)

(73) Assignees: Baxter International, Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 10/683,549

(22) Filed: Oct. 10, 2003

(65) Prior Publication Data

US 2005/0080011 A1 Apr. 14, 2005

(51) Int. Cl.
A61K 38/22 (2006.01)

(52) U.S. Cl. .................. 514/8; 424/85.1; 514/12; 514/21

(58) Field of Classification Search .............. 514/8, 514/12, 21, 773; 424/85.1
See application file for complete search history.

(56) References Cited

U.S. PATENT DOCUMENTS

| | | | |
|---|---|---|---|
| 4,703,008 A | 10/1987 | Lin | 435/240.2 |
| 4,992,419 A | 2/1991 | Woog et al. | 514/8 |
| 5,141,905 A | 8/1992 | Rosen et al. | 435/69.1 |
| 5,366,875 A | 11/1994 | Wozney et al. | 435/69.1 |
| 5,597,897 A * | 1/1997 | Ron et al. | 530/350 |
| 5,661,125 A | 8/1997 | Strickland | 514/8 |
| 5,688,679 A | 11/1997 | Powell | 435/240.2 |
| 5,705,482 A | 1/1998 | Christensen et al. | 514/12 |
| 5,919,757 A | 7/1999 | Michaelis et al. | 514/8 |
| 6,277,367 B1 | 8/2001 | Yamazaki et al. | 424/85.1 |
| 6,306,432 B1 * | 10/2001 | Shirley et al. | 424/450 |
| 6,328,728 B1 * | 12/2001 | Holladay et al. | 604/501 |
| 6,538,028 B1 * | 3/2003 | Pierson et al. | 514/564 |
| 6,605,699 B1 | 8/2003 | Ni et al. | 530/350 |
| 6,624,289 B1 * | 9/2003 | Bajaj | 530/328 |
| 2002/0055582 A1 | 5/2002 | Murakami et al. | 524/493 |
| 2002/0058608 A1 * | 5/2002 | Cormier et al. | 514/2 |
| 2003/0092622 A1 | 5/2003 | Sato et al. | 514/12 |
| 2003/0162711 A1 * | 8/2003 | Bjorn et al. | 514/12 |
| 2004/0166572 A1 * | 8/2004 | Wan et al. | 435/184 |
| 2005/0288222 A1 * | 12/2005 | Hayward et al. | 514/11 |

FOREIGN PATENT DOCUMENTS

| | | |
|---|---|---|
| EP | 0 909 564 A1 | 4/1999 |
| WO | WO 00/61169 A1 | 10/2000 |
| WO | WO 01/24814 A1 | 4/2001 |
| WO | WO 01/60420 A1 * | 8/2001 |
| WO | WO 01/64241 A1 * | 9/2001 |
| WO | WO 02/14356 A2 | 2/2002 |
| WO | WO 02/014356 A3 | 2/2002 |
| WO | WO 03/020299 A1 | 3/2003 |

OTHER PUBLICATIONS

Webster's II New Riverside University Dictionary. Boston: Houghton Mifflin Company.1984, p. 854.*
Dugas, H., et al., "Chemical Synthesis of Proteins," Bioorganic Chemistry of the Amino Acids, 1981, pp. 54-92, Springer-Verlag, New York.
Harris, S., et al., "Effects of Transforming Growth Factor β on Bone Nodule Formation and Expression of Bone Morphogenetic Protein 2, Osteocalcin, Osteopontin, Alkaline Phosphatase, and Type I Collagen mRNA in Long-Term Cultures of Fetal Rat Calvarial Osteoblasts," Journal of Bone and Mineral Research, 1994, pp. 855-863, vol. 9, No. 6, Mary Ann Liebert, Inc.
Nimtz, et al., "Structures of Sialylated Oligosaccharides of Human Erythropoietin Expressed In Recombinant BHK-21 Cells," Eur. J. Biochem., 1993, pp. 39-56, vol. 213.
Storring, P., et al., "Epoetin Alfa and Beta Differ in Their Erythropoietin Isoform Compositions and Biological Properties," British Journal of Haematology, 1998, pp. 79-89, vol. 100.
Sytkowski, A., et al., "Biological Activity and Structural Stability of N-Deglycosylated Recombinant Human Erythropoietin," Biochemical and Biophysical Research Communications, 1991, pp. 698-704, vol. 176, No. 2.
Tsuda, E., et al., "The Role of Carbohydrate in Recombinant Human Erythropoietin," Eur. J. Biochem., 1990, pp. 405-411, vol. 188.
Urist, M., "Bone: Formation by Autoinduction," Science, 1965, pp. 893-899, vol. 150.
Wozney, J., et al., "Novel Regulators of Bone Formation: Molecular Clones and Activities," Science, 1988, pp. 1528-1534, vol. 242.
Morlock, Michael, et al., "Erythropoietin Loaded Microspheres Prepared from Biodegradable LPLG-PEO-LPLG Triblock Copolymers: Protein Stabilization and In-Vitro Release Properties", Journal of Controlled Release 56, pp. 105-115 (1998).
International Search Report, PCT/US2004/031094, from the International Searching Authority dated Jan. 18, 2005.

* cited by examiner

Primary Examiner—Jeffrey Edwin Russel
(74) Attorney, Agent, or Firm—Senniger Powers (57) ABSTRACT

The present invention relates to stable pharmaceutical protein formulations that are stabilized using peptide stabilizers selected from the group consisting of Gly-Gly, Gly-Gly-Gly, Gly-Tyr, Gly-Phe, Gly-His, Gly-Asp, Gly-Ala, Ala-Gly, Ala-Ala, derivatives thereof and mixtures thereof. Furthermore, the present invention relates to stable pharmaceutical formulations comprising erythropoietin and peptide stabilizers selected from dipeptides, tripeptides, tetrapeptides, pentapeptides, and mixtures thereof. In addition to peptide stabilizers, the formulations may contain surfactants.

15 Claims, 3 Drawing Sheets

STABILIZATION OF PHARMACEUTICAL PROTEIN FORMULATIONS WITH SMALL PEPTIDES

FIELD OF THE INVENTION

The present invention relates to a stable pharmaceutical formulation comprising a biologically active protein and a peptide stabilizer. The invention further relates to a pharmaceutical formulation comprising erythropoietin and a stabilizer, wherein the stabilizer is a dipeptide, tripeptide, tetrapeptide, pentapeptide, or mixture thereof. The stable pharmaceutical formulations of the present invention may contain surfactants, such as Tween® 80.

BACKGROUND OF THE INVENTION

With the development of genetic recombination technology, a number of proteins have become available for therapeutic use. By way of example, proteins that are currently used to treat diseases include erythropoietin, Factor VIII, Factor IX, hemoglobin, insulin, interferons alpha, beta, and gamma, vascular endothelial growth factor, interleukin 2, and many others. However, proteins can lose biological activity as a result of physical instabilities (e.g., denaturation, formation of aggregates, etc.) and chemical instabilities, such as hydrolysis, oxidation, and deamidation. Stability of proteins is further influenced by factors such as pH, temperature, tonicity, and number of freeze-thaw cycles.

To ensure stability, therapeutic protein formulations are generally supplied either as a lyophilized protein to be dissolved just before use in a separately packaged water-soluble diluent, or as a protein solution containing additives for improving stability. For example, additives such as free amino acids (e.g., leucine, tryptophan, serine, arginine and histidine) useful in formulating protein solutions have been proposed in patents such as, e.g., AU 722300; U.S. Pat. Nos. 5,691,312; 6,120,761. Some protein formulations currently available on the market contain a protein as a stabilizer. For example, human serum albumin or purified gelatin are used to suppress chemical and physical changes in protein solutions. However, the addition of these proteins involves a complicated process for removing viral contamination. Lyophilization is another method used to ensure stability; however, this process increases manufacturing costs, and involves an increased risk of improper administration, as the lyophilized protein needs to be dissolved just prior to the use. U.S. Pat. No. 5,705,482 discloses a pharmaceutical solution of a human growth hormone (hGH) that is stabilized with the peptide Leu-His-Leu.

One of the proteins widely used as a therapeutic agent is erythropoietin. Erythropoietin is a 34–39 kDa glycoprotein hormone that stimulates the formation of red blood cells. It is produced in the kidney, and once produced, it circulates to the bone marrow where it stimulates the conversion of primitive precursor cells into proerythroblasts which subsequently mature into red blood cells. In the normal healthy state, erythropoietin is present in very low concentrations in plasma, i.e., about 0.01 to 0.03 U/ml, but when hypoxia occurs, i.e., the level of oxygen in transport is reduced, the kidney produces more erythropoietin. Hypoxia can be the result of e.g., the loss of large amounts of blood, destruction of red blood cells by radiation, or exposure to high altitudes. In addition, various forms of anemia cause hypoxia since red blood cells are responsible for oxygen transport in the body. In the normal state, an increased level of erythropoietin stimulates the production of new red blood cells thereby raising the level of oxygen and reducing or eliminating the hypoxic condition.

In contrast to this correction of hypoxia which occurs normally, patients with chronic renal failure ("CRF") have limited or no production of erythropoietin, and consequently, do not produce sufficient red blood cells. As the normal life span for red blood cells is about 120 days, such patients become increasing anemic with time. Prior to the development of recombinant erythropoietin, patients with chronic renal failure often had to undergo regular blood transfusions to maintain a minimum level of red blood cells.

There are several forms of erythropoietin currently used to treat patients—erythropoietin alpha, beta, omega, and delta. Erythropoietin omega is a recombinant protein expressed from the Apal fragment of human genomic erythropoietin DNA transformed into baby hamster kidney (BHK) cells. Erythropoietin omega and its expression are described in, e.g., U.S. Pat. No. 5,688,679. Furthermore, the structure and composition of carbohydrate residues in EPO omega has been described, e.g., in Nimtz et al., (*Eur. J. Biochem.*, 213:39, 1993) and Tsuda et al., (*Eur. J. Biochem.*, 188:405, 1990). EPO omega has an average molecular weight of about 35 kDa and is comprised of multiple isoforms (e.g., by isoelectric focusing, about 6–8 isoforms in broad cut fractions and 6 isoforms in peak fractions)), which is indicative of differing types and amounts of glycosylation, and in particular, different amounts of sialylation. EPO omega has an O-linked oligosaccharide content of less than 1 mole per mole of glycoprotein and has three N-glycosylation sites at amino acid residues Asn-24, Asn-38, and Asn-83 and an O-glycosylation site at amino acid residue Ser-126. Furthermore, unlike urinary human erythropoietin or erythropoietin alpha or beta, EPO omega retains substantially all of its in vivo biological activity even after being subjected to conditions that lead to substantial, if not complete N-deglycosylation, as reported in Sytkowski et al. (*Biochem. Biophys. Res. Commun.*, 176(2):698–704, 1991).

Although commercially available EPO formulations are generally well tolerated and stable, under extreme conditions, such formulations may be unstable and undergo activity losses. These activity losses can be attributed to a destruction of the EPO by catalytic effects of the surface of the ampule used for storage due to traces of heavy metals, atmospheric oxygen and the like, and also, to a deposition of EPO molecules on the vessel wall, a partial denaturing thereof possibly also taking place. Considering the fact that only a few micrograms are present in each dosage unit, the losses due to adsorption can be considerable, even after a short storage time. Furthermore, activity losses may be accelerated by external factors such as heat and light, or in formulations that are free of human blood products such as albumin, or in multi-dose formulations which contain preservatives such as benzyl alcohol.

Accordingly, pharmaceutical protein formulations, which exhibit improved stability without the need to lyophilize a desired protein or use human proteins as stabilizers are desirable.

SUMMARY OF THE INVENTION

In one embodiment, the present invention relates to a stable pharmaceutical protein formulation, wherein the formulation comprises a biologically active protein and a peptide stabilizer selected from the group consisting of Gly-Gly, Gly-Gly-Gly, Gly-Tyr, Gly-Phe, Gly-His, Gly- Asp, Gly-Ala, Ala-Gly, Ala-Ala, derivatives thereof and mixtures thereof, and wherein the formulation is free of human serum albumin.

In another embodiment, the present invention relates to a stable pharmaceutical protein formulation, wherein the formulation comprises erythropoietin and a peptide stabilizer selected from the group consisting of dipeptides, tripeptides, tetrapeptides, pentapeptides, and mixtures thereof, wherein the formulation is free of human serum albumin.

In still another embodiment provided is a stable pharmaceutical composition comprising erythropoietin, a peptide stabilizer selected from the group consisting of Gly-Gly, Gly-Gly-Gly, Gly-Tyr, Gly-Phe, Gly-His, Gly-Asp, Gly-Ala, Ala-Gly, Ala-Ala, derivatives thereof and mixtures thereof, and Tween® 80, and wherein the composition is free of human serum albumin.

Other objects and features will be in part apparent and in part pointed out hereinafter.

DETAILED DESCRIPTION OF THE INVENTION

The present invention provides stable pharmaceutical protein formulations, wherein the stabilization of such formulations is achieved by utilizing small peptides. The pharmaceutical protein formulations described herein are safe preparations, which are free of foreign proteins. Small peptides used as stabilizers in formulations described herein are cheaper than the conventional stabilizers, and the cost incurred during the manufacturing process is also lower than that for a lyophilized product. Furthermore, by utilizing small peptides, the pharmaceutical protein formulations avoid the addition of human serum albumin or other human or animal proteins such as gelatin, which may contain viral contaminants.

A protein for incorporation into a composition described herein may be any protein that has a therapeutic value in human subjects. Accordingly, such proteins include, without limitation, erythropoietin (EPO), Factor VIII, Factor IX, granulocyte colony stimulating factor (GCSF), granulocyte macrophage colony stimulating factor (GMCSF), thrombopoietin, heparin, interferons alpha, beta and gamma, interleukin 2, follicle stimulating factor, insulin-like growth factor (IGF), nerve growth factor (NGF), tumor necrosis factor (TNF), and bone morphogenetic family proteins (BMPs). The BMPs are novel factors in the extended transforming growth factor beta (TGF-β superfamily). They were first identified by Wozney J. et al. Science (1988) 242:1528–34, using gene cloning techniques, following earlier descriptions characterizing the biological activity in extracts of demineralized bone (Urist M. Science (1965) 150:893–99). These factors are expressed by normal osteoblasts as they differentiate, and have been shown to stimulate osteoblast differentiation and bone nodule formation in vitro as well as bone formation in vivo (Harris S. et al. J. Bone Miner Res (1994) 9:855–63). This latter property suggests potential usefulness as therapeutic agents in diseases which result in bone loss. The bone morphogenetic proteins (BMPs) include mammalian osteogenic protein-1 (OP-1, also known as BMP-7, and the Drosophila homolog 60A), osteogenic protein-2 (OP-2, also known as BMP-8), osteogenic protein-3 (OP-3, also known as BMP-8B), BMP-2 (also known as BMP-2A, and the Drosophila homolog DPP), BMP-3, BMP-4 (also known as BMP-2B), BMP-5, BMP-6 and its murine homolog Vgr-1, BMP-9, BMP-10, BMP-11, BMP-12, GDF-3 (also known as Vgr2), GDF-8, GDF-9, GDF-10, GDF-11, GDF-12, BMP-13, BMP-14, BMP-15, GDF-5 (also known as CDMP-1), GDF-6 (also known as CDMP-2), and GDF-7 (also known as CDMP-3 or BMP-12).

All of the proteins specified above are well known in the art, and their recombinant construction is well within the knowledge of one of ordinary skill in the art. Furthermore, a skilled artisan can readily determine which additional proteins may be formulated according to the present invention.

In one embodiment, the protein is selected from the group consisting of erythropoietin, Factor VIII, Factor IX, granulocyte colony stimulating factor, granulocyte macrophage colony stimulating factor, interferon alpha, interferon beta, interferon gamma, interleukin 2, follicle stimulating hormone, insulin-like growth factor, nerve growth factor, BMP-2, BMP-4, BMP-7, and tumor necrosis factor. In another embodiment, the protein is BMP-7. DNA sequences encoding BMP-7 proteins are described in, e.g., U.S. Pat. No. 5,141,905, and methods for producing BMP-7 proteins are described in, e.g., U.S. Pat. No. 5,366,875.

In still another embodiment, the protein is erythropoietin. EPO for use in the composition of the present invention has substantially the same biological activity as that of mammalian, especially, human EPO, and includes naturally occurring EPO and EPO obtained by genetic recombination. EPO from genetic recombination includes EPO having the same amino acid sequence as that of naturally occurring EPO, or EPO with this amino acid sequence from which one or more of the amino acids have been deleted, or in which one or more of the amino acids have been substituted, or to which one or more amino acids have been added, and which, however, retains the above-mentioned biological activity. The EPO in the present invention may be produced by any methods, for example, a method comprising extraction from human urine, followed by separation and purification, in various manners; and a method involving, for example, production in E. coli, yeast, Chinese hamster ovary (CHO) cells, or baby hamster kidney (BHK) cells, followed by extraction, separation and purification in various manners. In one embodiment, EPO is a recombinant EPO produced in CHO cells. For production of EPO in these cells, see, e.g., U.S. Pat. No. 4,703,008. In another embodiment, EPO is a recombinant EPO made in BHK cells. Production of EPO in BHK cells is well known in the art. See, e.g., U.S. Pat. No. 5,688,679. In yet another embodiment, the erythropoietin is erythropoietin omega (for description of EPO omega, see, e.g., U.S. Pat. No. 5,688,679 and WO 02/14356).

The amount of a biologically active protein in the composition described herein is the amount needed to deliver a therapeutically effective amount of the protein per unit dose to achieve a desired result. Hence, the amount can vary based on a protein and a number of other factors, such as the type of disease to be treated, age of patient, severity of the disease, presence of other conditions, and so forth. A skilled artisan can readily determine the appropriate amount of the protein to be included in the composition.

In one embodiment, when the biologically active protein is erythropoietin, the concentration of EPO in a pharmaceutical formulation is between about 500 IU/ml and about 100,000 IU/ml. In another embodiment, the concentration of EPO is between about 1,000 IU/ml and about 50,000 IU/ml, and in yet another embodiment, it is between about 2,000 IU/ml and about 20,000 IU/ml. In a preferred embodiment, the concentration of EPO in a pharmaceutical formulation disclosed herein is about 10,000 IU/ml. For pediatric indications, EPO can be formulated at a concentration of about 1,000 IU/ml.

For treatment of patients, EPO omega may be administered initially at higher doses to increase hemoglobin levels, and later at smaller doses that are suitable for a maintenance period, where a dose is adjusted for prolonged and continuous therapy. EPO omega may be administered to patients at a dose of about 5 IU/kg to about 150 IU/kg one to three times a week, or about 10 IU/kg to about 75 IU/kg, one to two times a week. In another practice, EPO omega is administered at a dose of about 25 IU/kg to about 60 IU/kg, or about 25 IU/kg to about 35 IU/kg, two times per week. In yet another practice, EPO omega is administered at a dose of about 50 IU/kg to about 150 IU/kg, or about 75 IU/kg to about 100 IU/kg once per week.

The peptide stabilizers to be used in the compositions described herein include dipeptides, tripeptides, tetrapeptides, pentapeptides, and mixtures thereof. Exemplary peptides of the present invention include Gly-Gly, Gly-Gly-Gly, Gly-Tyr, Gly-Phe, Gly-His, Gly-Asp, Gly-Ala, Ala-Gly, Ala-Ala, derivatives thereof and mixtures thereof; however, other peptides may be used as well.

Peptides for use in the protein formulations may be purchased from a commercial supplier, if they are commercially available, or may be synthesized. The principles of solid phase chemical synthesis of peptides are well known in the art and may be found in general texts in the area. See, e.g., H. Dugas and C. Penney, BIOORGANIC CHEMISTRY, (1981) Springer-Verlag, New York, pgs. 54–92. For example, peptides may be synthesized by solid-phase methodology utilizing an Applied Biosystems 430A peptide synthesizer (commercially available from Applied Biosystems, Foster City Calif.) and synthesis cycles supplied by Applied Biosystems.

Furthermore, in designing small peptides to be used in formulations described herein, conservative amino acids substitutions can be applied. Amino acid substitutions in the peptides of the present invention can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged at physiological pH) amino acids such as aspartic acid and glutamic acid; (2) basic (positively charged at physiological pH) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine. It should be noted that changes which are not expected to be advantageous can also be useful if these result in the production of functional sequences. For example, by utilizing a principle of conservative amino acid substitutions, Gly-Ala can be replaced with, e.g., Ser-Leu, Thr-Leu, Thr-Ile, etc. A skilled artisan can readily determine the sequences of peptides with conservative amino acid substitutions.

Examples of amino acid residues for use in a small peptide of the invention can be selected from any of the naturally occurring amino acids such as proteogenic L-amino acids (i.e., the 20 amino acids normally incorporated into proteins) as well as D-amino acids and non-proteogenic amino acids. Non-proteogenic amino acids are generally metabolites or analogues of the proteogenic amino acids. Non-limiting examples of naturally occurring non-proteogenic amino acids include ornithine, taurine, hydroxyproline, hydroxylysine, norleucine, β-alanine, gamma amino butyric acid, selenocysteine, phosphoserine, pyroglutamic acid, and pyrrolysine. The amino acid may also be selected from non-naturally occurring amino acids. Non-naturally occurring amino acids include, but are not limited to, amino acid derivatives and analogs. Non-limiting examples of amino acid derivatives include selenomethionine, telluro-methionine, and p-aminophenylalanine, fluorinated amino acids (e.g., fluorinated tryptophan, tyrosine and phenylalanine), nitrophenylalanine, nitrobenzoxadiazolyl-L-lysine, deoxymethylarginine, and cyclohexylalanine. Amino acid analogs include chemically synthesized compounds having properties known in the art to be characteristic of amino acids, examples of which include, e.g., the tryptophan "analog" b-selenolo[3,2-b]pyrrolylalanine and the proline "analog" thiaproline (1,3-thiazolidine4-carboxylic acid). Additional amino acid derivatives include amino acid salts, acylated amino acids, and alpha-keto amino acids.

In one embodiment, the peptide stabilizers can contain amino acid salts. By way of example, such salts can be made of inorganic acids such as amino acid hydrochlorides or organic acids such as amino acetate. For example, a peptide containing an amino acid hydrochloride, such as L-histidine hydrochloride or L-alanine hydrochloride may be used. Amino acid hydrochlorides are commercially available or they may be produced as is known in the art. For example, Gly-His.HCl.H$_2$O, Gly-Ala.HCl.H$_2$O, Ala.HCl.H$_2$O-Gly, and Ala.HCl.H$_2$O-Ala.HCl.H$_2$O are some of the peptide stabilizer examples that utilize amino acid salts. In another embodiment, peptide stabilizers contain acylated amino acids and/or alpha-keto amino acids. In addition to the examples described above, a number of different peptides can be created utilizing the amino acids described above. By way of example and not of limitation, a dipeptide can contain an L-amino acid and a D-amino acid, an L-amino acid and an amino acid salt, a D-amino acid and an amino acid analog, an L-amino acid and an acylated amino acid, an L-amino acid and an alpha-keto amino acid, an acylated amino acid and an alpha-keto amino acid, two acylated amino acids, two L-amino acids, two amino acid salts, etc. A skilled artisan can readily recognize additional amino acid combinations not only for dipeptides, but for other small peptides of the invention, as well.

The pharmaceutical formulations can include either a single species of a peptide (e.g. Gly-Gly) or mixtures of peptides. By way of example, mixtures can include a dipeptide and a dipeptide (e.g. Gly-Gly, Gly-His), a dipeptide and a tripeptide (e.g. Ala-Ala and Gly-Gly-Gly), a tripeptide and a pentapeptide, two dipeptides and a tripeptide, and so forth.

The concentration of a peptide stabilizer or mixtures thereof in a stable pharmaceutical composition described herein is between about 0.01 g/L and about 10 g/L. In another embodiment, the concentration of the peptide stabilizer is between about 0.5 g/L and about 5 g/L. In still another embodiment, the concentration of the peptide stabilizer is about 1 g/L.

In one embodiment of the present invention, the stable pharmaceutical protein composition contains a surfactant. While not being bound to a particular theory, it is believed that the presence of a surfactant in the solution reduces the adhesion of a biologically active protein, such as EPO to the walls of the container, in which the formulation is stored. The amount of surfactant used in the formulations described herein ranges from about 0.0005% w/v to about 0.5% w/v. In one embodiment, the amount of surfactant, particularly Tween® 80 is 0.03% w/v. In another embodiment, the surfactant is suitable for parenteral administration.

Any surfactant which is pharmaceutically acceptable can be included in the composition of the invention. Such surfactants include, without limitation, nonionic surfactants (e.g., polyoxyalkylene sorbitan fatty acid esters, sorbitan fatty acid esters, alkylene glycol fatty acid esters, polyoxyalkylene fatty acid esters, fatty acid esters, polyoxyalkylene fatty acid ethers, $C_{16}$–$C_{24}$ fatty acids, fatty acid mono-, di- or poly-glycerides, polyoxyalkylene alkyl phenols, alkyl phenyl ethers, polyoxyethylene polyoxypropylene block copolymers, fatty amine oxides, fatty acid alkanolamides, alkyl cellulose, carboxyalkyl cellulose, polyoxyalkylene castor oil derivatives), anionic surfactants (e.g., alkyl sulfates, olefin sulfates, ether sulfates, monoglyceride sulfates, alkyl sulfonates, aryl sulfonates, olefin sulfonates, alkyl sulfosuccinates, aryl sulfosuccinates, including sodium lauryl sulfate, dioctyl sodium sulfosuccinate and dioctyl sodium sulfonate), cationic surfactants (e.g., benzalkonium salts, polyoxyalkylene alkylamines, alkylamines, alkanolamine fatty acid esters, quaternary ammonium fatty acid esters, dialkyl ammonium salts, alkyl pyridinium salts including stearylamine, triethanolamine oleate, benzethonium chloride), amphoteric surfactants (e.g., alkyl β-aminopropionates, 2-alkylimidazoline quaternary ammonium salts) and zwitterionic surfactants. Nonionic surfactants for use in compositions of the invention include, but are not limited to, polyoxyethylene(20) sorbitan monolaurate (Tween® 20), polyoxyethylene(4) sorbitan monolaurate (Tween® 21), polyoxyethylene(20) sorbitan monopalmitate (Tween® 40), polyoxyethylene(20) sorbitan monostearate (Tween® 60), polyoxyethylene(20) sorbitan tristearate (Tween® 65), polyoxyethylene(20) sorbitan monooleate (Tween® 80 or polysorbate 80), or polyoxyethylene(20) sorbitan trioleate (Tween® 85), lauromacrogol 400, polyoxyl 40 stearate, polyoxyethylene hydrogenated castor oil 10, 50 and 60, glycerol monostearate, glycerol monooleate, polysorbate 40, 60, 65 and 80, sucrose fatty acid ester, sorbitan laurate, sorbitan oleate, sorbitan palmitate, sorbitan stearate, sorbitan tristearate, sorbitan sesquioleate, sorbitan trioleate, sorbitan isostearate, propylene glycol monostearate, polyoxyethylene monostearate, polyoxyethylene distearate, glyceryl monostearate, polyoxyethylene lauryl ether, polyoxyethylene cetyl ether, polyoxyethylene stearyl ether, polyoxyethylene oleyl ether, palmitic acid, stearic acid, oleic acid, ethyl oleate, isopropyl myristate, sodium palmitate, sodium stearate, sodium oleate, nonylphenol polyethoxyethanols, tributylphenoxy-polyethoxyethanol, octylphenoxy-polyethoxyethanol, polyoxyethylene glycerol trinicinoleate or polyoxyl 35 castor oil (Cremophor® EL, BASF Corp.), polyoxyethylene glycerol oxystearate (Cremophor® RH 40), polyethylene glycol 60 hydrogenated castor oil (Cremophor® RH 60), Poloxamer® 124, Poloxamer® 188, Poloxamer® 237, Poloxamer® 388, Poloxamer® 407 (BASF Wyandotte Corp.), methylcellulose and carboxymethyl cellulose. Preferably, the surfactant used is a polyoxyethylene sorbitan mono- or tri-lauryl, palmityl, stearyl or oleyl ester such as polyoxyethylene(20) sorbitan monolaurate (Tween® 20), polyoxyethylene(4) sorbitan monolaurate (Tween® 21), polyoxyethylene(20) sorbitan monopalmitate (Tween® 40), polyoxyethylene(20) sorbitan monostearate (Tween® 60), polyoxyethylene(20) sorbitan tristearate (Tween® 65), polyoxyethylene(20) sorbitan monooleate (Tween® 80 or polysorbate 80), or polyoxyethylene(20) sorbitan trioleate (Tween® 85).

Optionally, the stable pharmaceutical protein formulations described herein may include preservatives, buffering agents, isotonicity agents, and other conventional components used in formulating pharmaceutical compositions.

In one embodiment, the preservatives useful in the compositions of the present invention are those preservatives compatible with, e.g., erythropoietin so that the compositions are stable. Particular preservatives contemplated for use include benzyl alcohol, parabens, phenol, phenol derivatives, benzalkonium chloride and mixtures thereof. Depending on the particular preservative utilized, the amount of preservative could vary. For example, benzyl alcohol is used in the amount of 0.6–2.0%, preferably in the amount of about 1%. At this concentration, benzyl alcohol provides the preservative and the local anesthetic capacities without unduly affecting the stability of the erythropoietin.

In another embodiment, a buffering agent is used to maintain the pH of the composition within a desired range. Preferred agents include various salt, acidic, or basic forms of the following anions: citrate, phosphate, tartrate, succinate, adipate, maleate, lactate, acetate, bicarbonate, pyruvate, and carbonate. Representative salts of these buffers which may be used are the sodium and potassium forms, as long as the salt and the amount are physiologically compatible in an injectable composition. Mixtures of these buffering agents may also be used. Among these agents, citrate and phosphate buffers are desirable. The amount of buffering agent useful in the pharmaceutical compositions depends largely on the particular buffer used and the pH of the solution. For example, citrate is a more efficient buffer at pH 6 than at pH 7 so less citrate may be used in a solution at pH 6 than at pH 7. The preferred pH range for the solutions is about 5–8, with about 6–7.5 being more preferred, and a pH of about 7 being most preferred. Over these pH values, the amount of buffers will generally range from about 1 mM to about 30 mM. The amount of citrate buffer may range from about 1 mM to about 20 mM. The same preservatives, buffering agents, and isotonicity agents may be used for proteins other than erythropoietin; however, it may be necessary to adjust pH or concentrations of additives. These modifications can be determined by routine experimentation.

The compositions of the present invention may further include an isotonicity adjusting agent to render the solution isotonic and more compatible for injection. The preferred agents include sodium chloride, glycerol, mannitol, sucrose, sorbitol and mixtures thereof. The most preferred agent is sodium chloride. The amount of isotonicity adjusting agent needed to render the solution isotonic varies with the particular agent but generally falls within the range of about 0.1–10%.

In one embodiment, the pharmaceutical protein formulations are prepared by adding a peptide stabilizer or a mixture of two or more stabilizers to a sterile phosphate buffered saline (PBS) solution. The pH of the solution is preferably about pH 7.2. If a surfactant is utilized, e.g., Tween® 80, it can be added with the peptide stabilizer. Following this, the solution is mixed well, and a biologically active protein, e.g., EPO is added to the solution. Optionally, if additional agents such as buffering agents or preservatives are used, they may be added either prior to the addition of the protein or following protein addition.

The stable pharmaceutical protein formulations may be contained in a sealed, sterilized plastic or glass container. The solution preparation can be supplied as a prescribed dose in an ampule, vial or disposable syringe, or in a multiple dose form such as a bag or bottle for injection. In one embodiment, the stable pharmaceutical protein formulations can be stored at refrigerated conditions for at least 24 months.

The stable protein formulations of the present invention are generally administered by a parenteral route, e.g., by injection (intramuscular, intraperitoneal, subcutaneous, or intravenous); however, the formulations may also be administered by other routes, such as percutaneously, transmucosally or transnasally.

The stable pharmaceutical protein formulations described herein can be used to treat any condition for which a protein that is in the formulation is indicated. By way of example and not of limitation, when the protein in the formulation is erythropoietin, the formulation can be used to treat any condition in which stimulation of red blood cell (RBC) proliferation is desired. Thus, EPO can be used to treat anemia, wherein anemia is associated with endogenous erythropoietin deficiency, anemia of malignant disease, anemia resulting from a chemotherapeutic/radiation treatment of a malignant disease, or anemia of chronic disease. Anemias of chronic disease include but are not restricted to anemia associated with rheumatoid arthritis, hepatitis, AIDS (especially in patients treated with AZT), anemia of prematurity, anemia associated with renal failure, anemia of thalassemia, autoimmune hemolytic anemia, aplastic anemia, and anemia associated with surgery (e.g., to increase erythropoiesis in patients undergoing bone marrow transplantation).

In another example, when a protein is a BMP family member such as BMP-7, it can be used to treat a plethora of conditions, which are characterized by the need to enhance bone formation. These conditions include, e.g., bone fractures, where it is desirable to stimulate bone growth and to hasten bone repair. Other bone deficit conditions that can be treated with BMP protein formulated as described herein include, without limitation bone segmental defects, periodontal disease, metastatic bone disease, osteolytic bone disease and conditions where connective tissue repair would be beneficial, such as healing or regeneration of cartilage defects or injury. Other conditions characterized by the need for bone growth include primary and secondary hyperparathyroidism and osteoporosis (including age-related osteoporosis, osteoporosis associated with post-menopausal hormone status, disuse osteoporosis, diabetes-related osteoporosis, and glucocorticoid-related osteoporosis). Alternatively, BMP family members as formulated herein may be used to modulate metabolism, proliferation and/or differentiation of normal or aberrant cells or tissues.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the present invention.

All publications and patent applications cited in this specification are herein incorporated by reference as if each individual publication or patent application was specifically and individually indicated to be incorporated by reference.

Abbreviations and Definitions

To facilitate understanding of the invention, a number of terms are defined below:

"BMP" is an abbreviation for bone morphogenetic protein.

"CDMP" is an abbreviation for cartilage-derived morphogenetic protein.

"DPP" stands for decapentaplegeic protein.

"GDF" is an abbreviation for growth and differentiation factor.

"OP" is an abbreviation for osteogenic protein.

"Vgr" is an abbreviation for vegetal (protein) related.

"RH" is an abbreviation for relative humidity.

"HSA" is an abbreviation for human serum albumin.

"AUC" is an abbreviation for area under curve.

As used herein, the term "amino acid" is used in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids.

As used herein, "biologically active protein" refers to the ability of a protein to perform substantially the same function as the native form of the protein of interest.

"Composition" and "formulation" are used interchangeably herein.

As used herein, "peptide" means a compound that consists of two or more amino acids that are linked by means of at least one peptide bond. "Dipeptide" means a peptide consisting of two amino acids connected by a peptide bond, "tripeptide" means a peptide consisting of three amino acids connected by peptide bonds, and so forth. "Small peptides" for purposes of the present invention includes dipeptides, tripeptides, tetrapeptides, and pentapeptides.

The terms "stable" and "stabilized" mean that a pharmaceutical composition of the invention has increased storage stability relative to the same composition, which does not comprise any peptide stabilizers as described herein. The stabilization provided by the present invention allows for increased storage stability in liquid form at 2°–8° C., ease of administration without reconstitution, and ability to supply the formulation in prefilled, ready-to-use syringes or as multidose preparations if the formulation is compatible with bacteriostatic agents. Preferably, the stable compositions of the invention can be stored at refrigerated conditions (between about 2' and about 8° C.) for at least 6 months, 12 months, 18 months, 24 months, 30 months, 36 months, or more.

The phrase "therapeutically effective" is intended to qualify the amount of a biologically active protein, which will achieve the goal of improvement in disease severity and the frequency of incidence over treatment, while avoiding adverse side effects typically associated with alternative therapies.

An "IU" or "international unit" is a standardized measurement of the amount of a specified biological effect of a drug or naturally occurring material. In particular, an IU for erythropoietin refers to unit measurement from an in vivo ex-hypoxic polycythaemic mouse assay that is standardized using the World Health Organization's International Reference Preparation of erythropoietin. The amount of material required to provide one IU for a given material will vary with the source, condition, quality, purity, and/or type of material. The relationship between IUs and other units such as defined by radioimmune assays, may be further understood by reference to Storring et al., *Brit. J. Haematol.*, 100:79, 1998.

The following examples illustrate the invention, but are not to be taken as limiting the various aspects of the invention so illustrated.

EXAMPLE 1

The present study was designed to evaluate the stability of erythropoietin omega in a PBS solution containing 1) small peptides or 2) small peptides and Tween® 80 as stabilizers. The stability was evaluated in comparison to stability of EPO omega when either no stabilizers were used or when human serum albumin (HSA) or Tween® 80 were used alone as stabilizers. The following small peptides were used in the study: Gly-Gly, Gly-Gly-Gly, Gly-Tyr, Gly-Phe, Gly-His.HCl.$H_2O$, Gly-Asp, Gly-Ala, Ala-Gly and Ala-Ala. All of the peptides and Tween® 80 were purchased from Sigma-Aldrich.

The protocols listed below were applied to prepare solutions that were used to assess storage stability of pharmaceutical formulation containing erythropoietin omega:

To prepare a PBS solution, into a glass bottle add water for injection (WFI) to approximately 800 g;

add 8.18 g of NaCl and 1.56 g of $NaH_2PO_4.2H_2O$;

add WFI with stirring up to the total formulated solution mass, 1006 g;

stir rapidly for a minimum of 15 minutes (all of the salt should be dissolved prior to the end of mixing);

introduce nitrogen into the solution; bubble for 2 minutes;

determine the pH of the solution and adjust to 7.20 (range 7.10 to 7.30) with 10M NaOH;

filter the solution through a sterile 0.22 μm membrane filter into the sterile container; and use the filtered solution to prepare formulated solutions of erythropoietin.

To make a stock solution of PBS pH 7.2—peptide (1.25 g/L), combine PBS pH 7.2 (50 ml) and a peptide (62.5 mg).

To make a stock solution of PBS pH 7.2—Tween® 80 (0.375 g/L), combine PBS pH 7.2 (1000 ml) and Tween® 80 (0.375 g).

To make a stock solution of PBS pH 7.2—peptide (1.25 g/L)—Tween® 80 (0.375 g/L), add to 50 ml of the PBS pH 7.2—Tween® 80 (0.375 g) stock solution a peptide (62.5 mg).

To make a stock solution of EPO (50,000 IU/ml) in PBS pH 7.2, combine PBS pH 7.2 (75.3 ml) and 14.7 ml of EPO concentrate solution (306,000 IU/ml).

To make a solution of EPO 10,000 IU/ml in PBS pH 7.2, mix 16 ml of PBS pH 7.2 and 4 ml of stock EPO (50,000 IU/ml).

To make a solution of EPO 10,000 IU/ml in PBS pH 7.2—HSA 2.5 mg/L, mix 16 ml of PBS pH 7.2, 4 ml of stock EPO (50,000 IU/ml) and 250 μl HSA (20% w/v).

To make a solution of EPO 10,000 IU/ml in PBS pH 7.2—Tween® 80 (0.3 g/L), mix 16 ml of PBS pH 7.2—Tween® 80 stock solution and 4 ml of stock EPO (50,000 IU/ml).

To make a solution of EPO 10,000 IU/ml in PBS pH 7.2—peptide (1.0 g/L), mix 16 ml of PBS pH 7.2—peptide stock solution and 4 ml of stock EPO (50,000 IU/ml).

To make a solution of EPO 10,000 IU/ml in PBS pH 7.2—Tween® 80 (0.3 g/L)—peptide (1.0 g/L), mix 16 ml of PBS pH 7.2—Tween® 80—peptide stock solution and 4 ml of stock EPO (50,000 IU/ml).

All solutions are well mixed to ensure homogenization and filtered through sterile 0.22 μm membrane filter into sterile containers.

Table 1 describes EPO samples used in this study.

TABLE 1

| Sample | EPO IU/ml | Surfactant | Surfactant Conc. mg/ml | Peptide | Peptide Conc. mg/ml |
|---|---|---|---|---|---|
| B001 | 10,000 | No | n/a | Albumin | 2.5 |
| B002 | 10,000 | No | n/a | No | n/a |
| B003 | 10,000 | Tween® 80 | 0.3 | No | n/a |
| B004 | 10,000 | No | n/a | Gly-Gly | 1 |
| B005 | 10,000 | No | n/a | Gly-Gly-Gly | 1 |
| B006 | 10,000 | No | n/a | Gly-Tyr | 1 |
| B007 | 10,000 | No | n/a | Gly-Phe | 1 |
| B008 | 10,000 | No | n/a | Gly-His | 1 |
| B009 | 10,000 | No | n/a | Gly-Asp | 1 |
| B010 | 10,000 | No | n/a | Gly-Ala | 1 |
| B011 | 10,000 | No | n/a | Ala-Gly | 1 |
| B012 | 10,000 | No | n/a | Ala-Ala | 1 |
| B013 | 10,000 | Tween® 80 | 0.3 | Gly-Gly | 1 |
| B014 | 10,000 | Tween® 80 | 0.3 | Gly-Gly-Gly | 1 |
| B015 | 10,000 | Tween® 80 | 0.3 | Gly-Tyr | 1 |
| B016 | 10,000 | Tween® 80 | 0.3 | Gly-Phe | 1 |
| B017 | 10,000 | Tween® 80 | 0.3 | Gly-His | 1 |
| B018 | 10,000 | Tween® 80 | 0.3 | Gly-Asp | 1 |
| B019 | 10,000 | Tween® 80 | 0.3 | Gly-Ala | 1 |
| B020 | 10,000 | Tween® 80 | 0.3 | Ala-Gly | 1 |
| B021 | 10,000 | Tween® 80 | 0.3 | Ala-Ala | 1 |

The samples were initially kept at 25° C./60% RH, and analyzed at weeks 1, 2, 4, 6, 8, and 10. After 4 weeks of storage, 2 sets of samples were transferred to 40° C./60% RH and analyzed at weeks 6 and 8. This was done in order to stress the solution to a greater extent in order to magnify any potential stabilizer effect. The study at 25° C./60% RH was discontinued after 10 weeks.

Solutions were analyzed by high pressure liquid chromatography (HPLC) using separation module WATERS® ALLIANCE 2690 equipped with a WATERS oven and a WATERS® Dual λ Absorbance detector. The system was connected to a WATERS® C4-300 Å-5 μm DELTA-PACK column. Samples were transferred into HPLC vials using sterile 1.0 ml KENALL Monoject syringes equipped with 23G×1¼" sterile KENDALL Monoject needles. The protein content was measured as the peak AUC at 280 nm.

The Area Under Curve (AUC) was recorded and used to calculate the recovery of protein based on the response at the initial period. The recovery was calculated as the ratio between the response at the period of interest and at the initial period.

Recovery$_{AUC}$(%)=100×C$_{AUC\ t}$/C$_{AUC\ 0}$, wherein

Recovery$_{AUC}$ is recovery based on AUC,

C$_{AUC\ t}$ is erythropoietin content at the period of interest expressed as the AUC of the peak, and C$_{AUC\ 0}$ is erythropoietin content at the initial period expressed as the AUC of the peak.

Prior to the study initiation, the absence of interference between potential degradation products coming from the peptide stabilizers and erythropoietin omega was investigated. This was another experiment control designed to evaluate if small peptides and/or Tween® 80 can affect proper calculation of AUC and recovery % for EPO. To address this issue, solutions containing small peptides and no erythropoietin omega were kept for 4 weeks at 25° C./60% RH and 4 weeks at 40° C./60% RH before injection. Analysis of the chromatograms showed that no signal was visible in the neighborhood of erythropoietin omega signal (20.6 min.), indicating that peptides and/or Tween® 80 do not affect calculation of AUC and recovery % for EPO.

Figure 1:
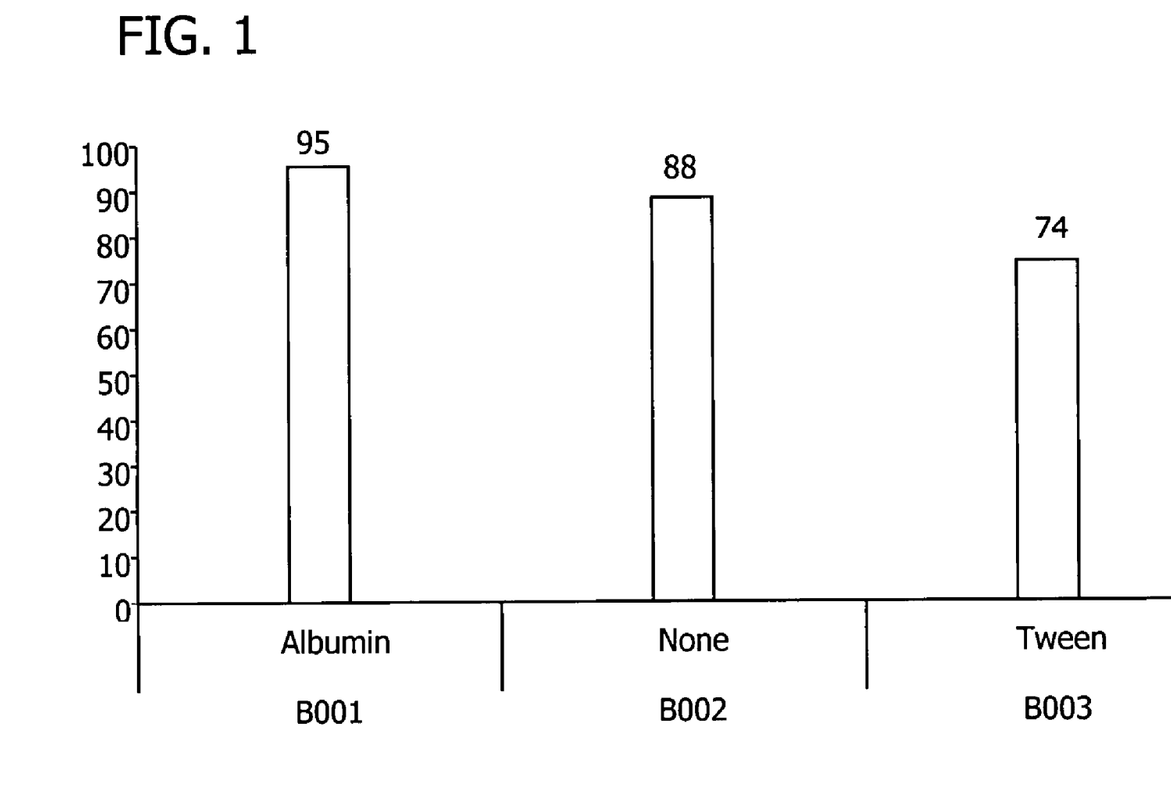
FIG. 1 depicts EPO recovery (%) after incubation for 4 weeks at 25° C. and 4 weeks at 40° C. alone (B002) or in the presence of HSA (B001) or Tween® 80 (B003) after 8 weeks of incubation, as described in Example 1.
Figure 2:
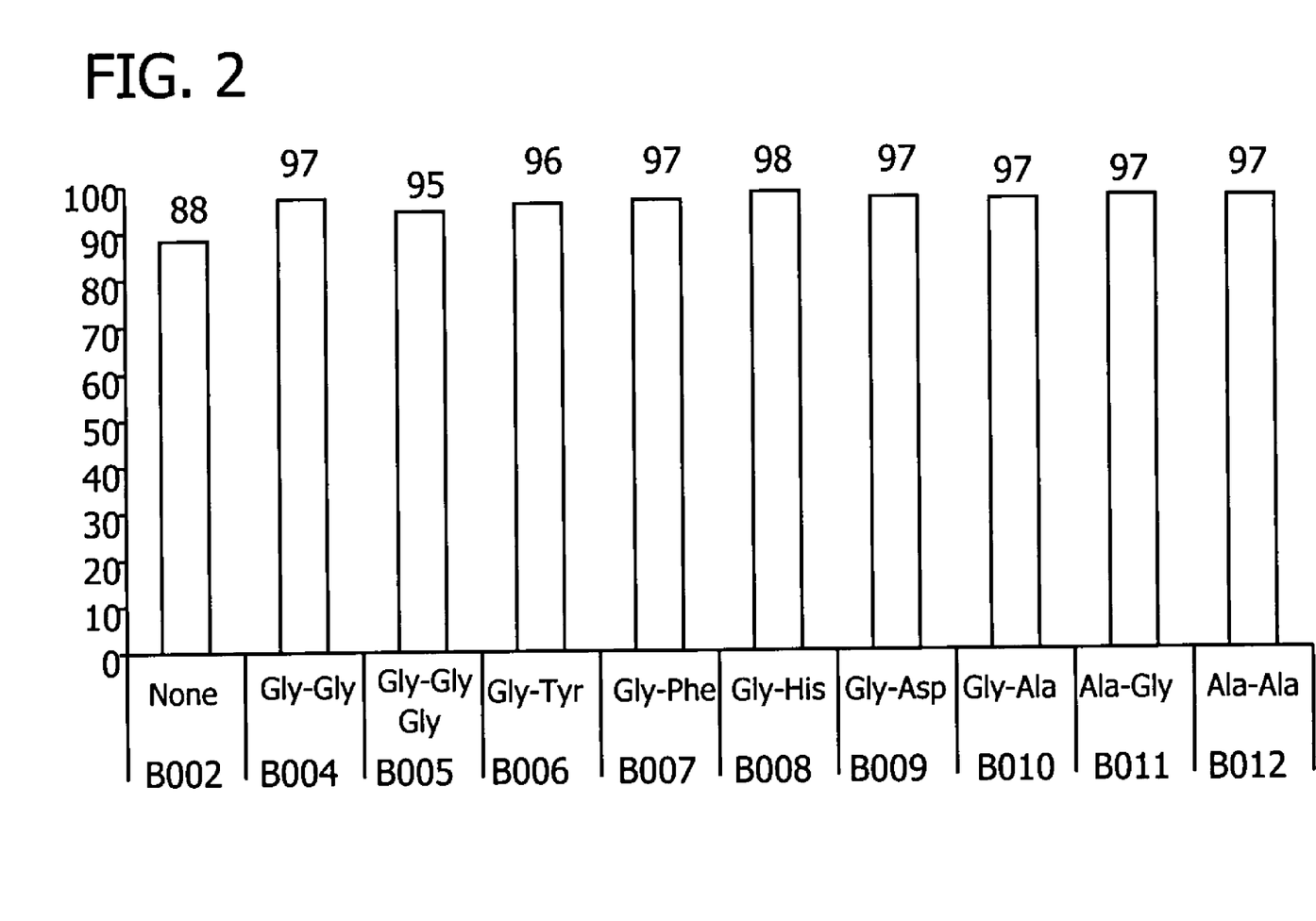
FIG. 2 depicts EPO recovery (%) after incubation for 4 weeks at 25° C. and 4 weeks at 40° C. in the presence of a peptide stabilizer (B004–B0012) after 8 weeks of incubation, as described in Example 1.
Figure 3:
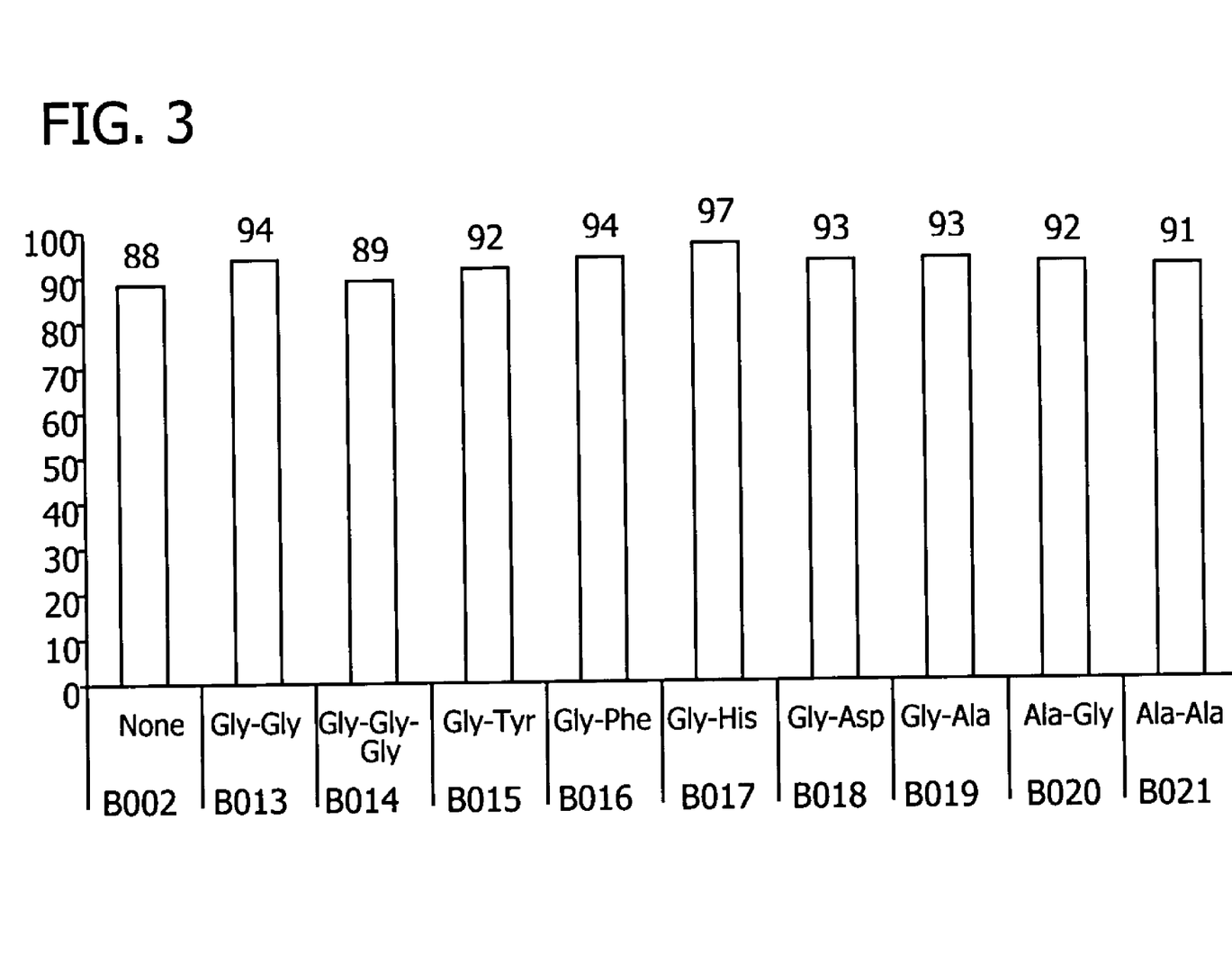
FIG. 3 depicts EPO recovery (%) after incubation for 4 weeks at 25° C. and 4 weeks at 40° C. in the presence of a peptide stabilizer and Tween® 80 (B013–B021) after 8 weeks of incubation, as described in Example 1.

Table 2 (see below) shows % recoveries of EPO when stabilized with small peptides (B004–B012) or small peptides and Tween® 80 (B013–B021) at 25° C./60% RH at weeks 1, 2, 4, 6, 8, and 10 and at 40° C./60% RH at weeks 6 and 8. As can be seen from the table, except for control solutions containing EPO alone (B002) or Tween® (B003), almost no degradation was recorded in test samples stored at 25° C./60% RH for 10 weeks. At the same conditions, no protein degradation was recorded in EPO with HSA sample (B001). For the control solutions free of HSA (B002 and B003), a slight reduction was recorded with time. Furthermore, EPO stability at 40° C./60% RH was better in the samples containing a peptide or a peptide and Tween® stabilizer than in the control samples free of HSA kept at the same conditions. In addition, and as expected, the EPO solutions showed better storage stability at 25° C. than at 40° C. The same results can be seen as graphic representations in FIGS. 1, 2, and 3.

TABLE 2

| Sample | % Recovery of EPO @ 25° C./60% RH | | | | | | % Recovery of EPO @40° C./60% RH | |
|---|---|---|---|---|---|---|---|---|
| | w0 | w1 | w2 | w4 | w6 | w8 | w10 | w6 | w8 |
| B001 | 100 | 100 | 100 | 101 | 100 | 101 | 101 | 97 | 95 |
| B002 | 100 | 100 | 99 | 99 | 97 | 97 | 96 | 90 | 88 |
| B003 | 100 | 99 | 98 | 97 | 94 | 93 | 93 | 82 | 74 |
| B004 | 100 | 100 | 99 | 100 | 99 | 100 | 98 | 97 | 97 |
| B005 | 100 | 99 | 99 | 100 | 98 | 99 | 98 | 95 | 95 |
| B006 | 100 | 100 | 100 | 100 | 100 | 99 | 99 | 97 | 96 |
| B007 | 100 | 100 | 99 | 99 | 100 | 100 | 99 | 98 | 97 |
| B008 | 100 | 99 | 99 | 100 | 99 | 87* | 99 | 98 | 98 |
| B009 | 100 | 100 | 100 | 100 | 100 | 99 | 99 | 97 | 97 |
| B010 | 100 | 99 | 100 | 100 | 99 | 99 | 98 | 97 | 97 |
| B011 | 100 | 99 | 99 | 100 | 99 | 99 | 98 | 97 | 97 |
| B012 | 100 | 99 | 100 | 101 | 99 | 100 | 98 | 99 | 97 |
| B013 | 100 | 99 | 99 | 99 | 99 | 98 | 98 | 96 | 94 |
| B014 | 100 | 99 | 99 | 99 | 98 | 98 | 98 | 94 | 89 |
| B015 | 100 | 99 | 99 | 100 | 99 | 99 | 100 | 95 | 92 |
| B016 | 100 | 99 | 99 | 100 | 99 | 99 | 98 | 96 | 94 |
| B017 | 100 | 99 | 99 | 100 | 99 | 100 | 99 | 98 | 97 |
| B018 | 100 | 98 | 99 | 99 | 98 | 99 | 98 | 95 | 93 |
| B019 | 100 | 99 | 99 | 99 | 99 | 99 | 98 | 95 | 93 |
| B020 | 100 | 98 | 99 | 98 | 98 | 99 | 98 | 95 | 92 |
| B021 | 100 | 98 | 99 | 99 | 98 | 99 | 98 | 95 | 91 |

*After 8 weeks of storage at 25° C./60% RH, a recovery of 87% was found for B008. This out of trend result was not confirmed either at the following period or at 40° C./60% RH, and was due to an equipment issue (power supply failure).

It should be noted that all of the above-mentioned procedures can be modified for a particular study, depending on factors such as a protein used, length of the study, etc. Such modifications can be designed by a skilled artisan without undue experimentation.

What is claimed is:

1. A method of parenteral administration comprising administering a stable pharmaceutical composition to a patient by parenteral injection, wherein the composition comprises erythropoietin and a peptide stabilizer selected from the group consisting of Gly-Gly, Gly-Gly-Gly, Gly-Tyr, Gly-Phe, Gly-His, Gly-Asp, Gly-Ala, Ala-Gly, Ala-Ala, derivatives thereof and mixtures thereof, the composition is free of serum albumin and the derivatives are acylated, fluorinated, alpha-keto or salt forms of said peptide stabilizers, or include nitro Phe or p-amino Phe in place of Phe, or cyclohexyl Ala in place of Ala.

2. The method of claim 1, wherein the derivatives comprise salts of Gly-Gly, Gly-Gly-Gly, Gly-Tyr, Gly-Phe, Gly-His, Gly-Asp, Gly-Ala, Ala-Gly, and Ala-Ala.

3. The method of claim 1, wherein concentration of the peptide stabilizer in said composition is between about 0.01 g/L and about 10 g/L.

4. The method of claim 3, wherein the concentration of the peptide stabilizer is between about 0.5 g/L and about 5 g/L.

5. The method of claim 1, wherein the erythropoietin is a recombinant erythropoietin.

6. The method of claim 5, wherein the recombinant erythropoietin is produced in BHK cells.

7. The method of claim 5, wherein the recombinant erythropoietin is produced in CHO cells.

8. The method of claim 5, wherein the recombinant erythropoietin is erythropoietin omega.

9. The method of claim 8, wherein concentration of erythropoietin omega in said composition is between about 500 IU/ml and about 100,000 IU/ml.

10. The method of claim 9, wherein the concentration of erythropoietin omega is between about 2,000 IU/ml and about 20,000 IU/ml.

11. The method of claim 1, wherein the composition further comprises a surfactant.

12. The method of claim 11, wherein the surfactant is a nonionic surfactant, cationic surfactant, anionic surfactant, amphoteric surfactant, zwitterionic surfactant, or a mixture thereof.

13. The method of claim 11, wherein concentration of the surfactant in said composition is between about 0.0005% w/v and about 0.5% w/v.

14. A method of parenteral administration comprising administering a stable pharmaceutical composition to a patient by parenteral injection, wherein the composition comprises erythropoietin, a polyoxyalkylene sorbitan fatty acid ester, and a peptide stabilizer selected from the group consisting of Gly-Gly, Gly-Gly-Gly, Gly-Tyr, Gly-Phe, Gly-His, Gly-Asp, Gly-Ala, Ala-Gly, Ala-Ala, derivatives thereof and mixtures thereof, the composition is free of serum albumin and the derivatives are acylated, fluorinated, alpha-keto or salt forms of said peptide stabilizers, or include nitro Phe or p-amino Phe in place of Phe, or cyclohexyl Ala in place of Ala.

15. The method of claim 14, wherein the erythropoietin is erythropoietin omega.

* * * * *